(12) United States Patent
Zurschmiede et al.

(10) Patent No.: US 11,457,964 B2
(45) Date of Patent: Oct. 4, 2022

(54) VARIABLE ANGLE BONE PLATE SYSTEM

(71) Applicant: 41MEDICAL AG, Bettlach (CH)

(72) Inventors: Silas Zurschmiede, Bibern (CH); Patrick Burki, Solothurn (CH); Robert Frigg, Bettlach (CH)

(73) Assignee: 41MEDICAL AG, Bettlach (CH)

( * ) Notice: Subject to any disclaimer, the term of this patent is extended or adjusted under 35 U.S.C. 154(b) by 177 days.

(21) Appl. No.: 16/976,043

(22) PCT Filed: Feb. 27, 2018

(86) PCT No.: PCT/IB2018/051230
§ 371 (c)(1),
(2) Date: Aug. 26, 2020

(87) PCT Pub. No.: WO2019/166851
PCT Pub. Date: Sep. 6, 2019

(65) Prior Publication Data
US 2021/0369312 A1    Dec. 2, 2021

(51) Int. Cl.
*A61B 17/80* (2006.01)
*A61B 17/86* (2006.01)
(52) U.S. Cl.
CPC ...... *A61B 17/8057* (2013.01); *A61B 17/8061* (2013.01); *A61B 17/866* (2013.01)
(58) Field of Classification Search
CPC .................................................. A61B 17/8057
See application file for complete search history.

(56) References Cited

U.S. PATENT DOCUMENTS

| 6,206,881 | B1 | 3/2001 | Frigg et al. |
| 9,095,391 | B2 | 8/2015 | McKinley |
| 2004/0073218 | A1 | 4/2004 | Dahners |
| 2005/0165400 | A1 | 7/2005 | Fernandez |
| 2005/0261688 | A1 | 11/2005 | Grady, Jr. et al. |

(Continued)

FOREIGN PATENT DOCUMENTS

| EP | 3178423 A1 | 6/2017 |
| WO | 2011154891 A2 | 12/2011 |
| WO | 2017139903 A1 | 8/2017 |

OTHER PUBLICATIONS

Streicher et al. "New surface modification for Ti—6Al—7Nb alloy: oxygen diffusion hardening (ODH)" Biomaterials 1991, vol. 12.

*Primary Examiner* — Olivia C Chang
(74) *Attorney, Agent, or Firm* — Maschoff Brennan

(57) ABSTRACT

The invention concerns a bone plate system comprising: a bone fastening element comprising a shaft with a first thread with a first lead length, the fastening element further comprising a head with a second thread on its outer surface, the second thread having a second lead length, the outer surface having a first hardness; and a bone plate with a second hardness which is smaller than the first hardness, the bone plate comprising a non-threaded through hole in a non-assembled state for receiving the bone fastening element, the hole comprising a first hole portion with a first three-dimensional shape and a second hole portion with a second, different three-dimensional shape. The first lead length substantially equals the second lead length, and the second thread is arranged to irreversible deform the wall of the hole to form a female thread on the wall.

15 Claims, 6 Drawing Sheets

(56) References Cited

U.S. PATENT DOCUMENTS

| | | |
|---|---|---|
| 2009/0018588 A1 | 1/2009 | Eckhof et al. |
| 2009/0292318 A1 | 11/2009 | White et al. |
| 2010/0168841 A1 | 7/2010 | Furst et al. |
| 2014/0005728 A1 | 1/2014 | Koay et al. |
| 2014/0018862 A1* | 1/2014 | Koay .................. A61B 17/866 606/291 |
| 2016/0022879 A1 | 1/2016 | Foran |
| 2016/0199111 A1 | 7/2016 | Knoepfle et al. |
| 2018/0049782 A1 | 2/2018 | Gahman et al. |

* cited by examiner

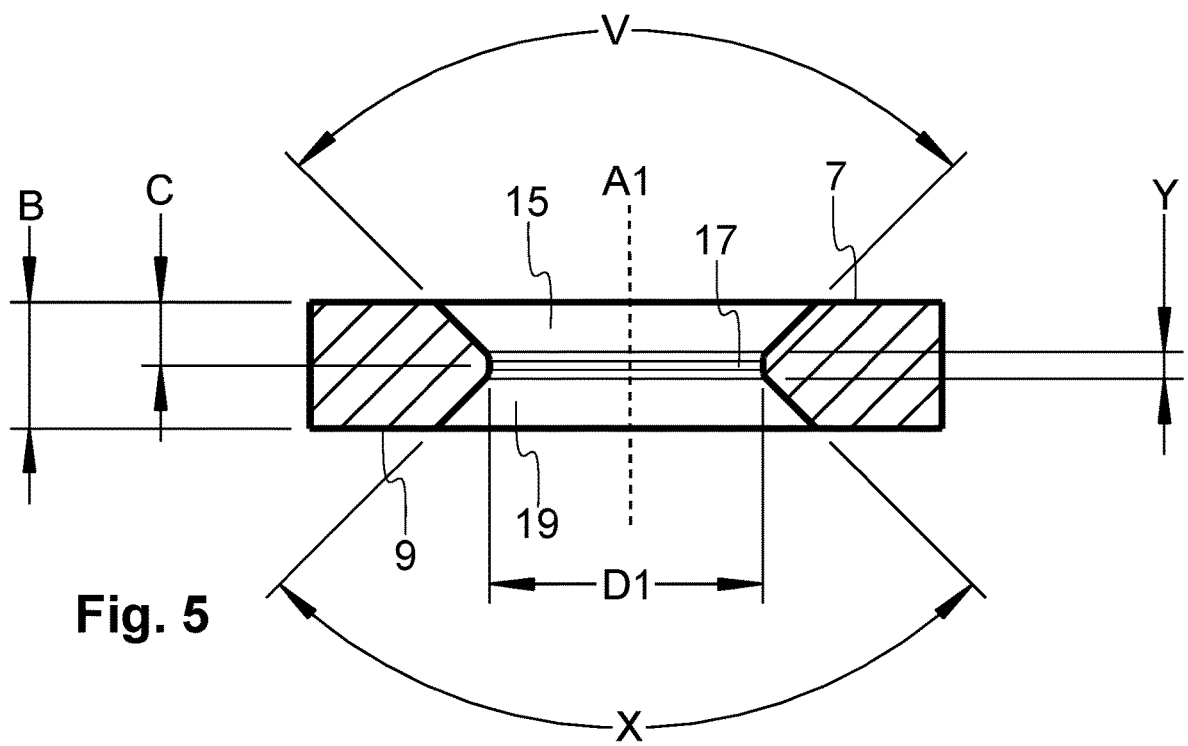
Fig. 5
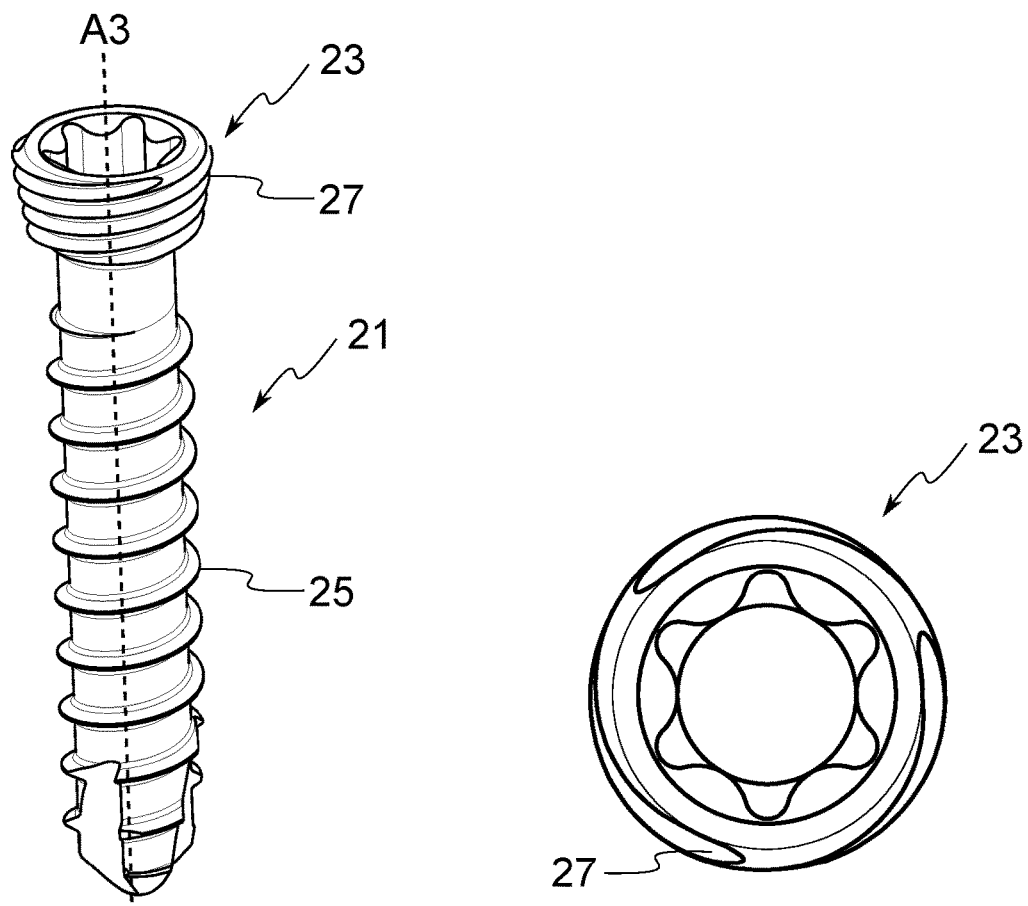
Fig. 6
Fig. 7

VARIABLE ANGLE BONE PLATE SYSTEM

TECHNICAL FIELD

The present invention relates to a bone plate system comprising a bone plate and a fastening element, such as a screw. More specifically, when screwing the fastening element into the bone plate, the angle between the fastening element and the bone plate can be defined by a user.

BACKGROUND OF THE INVENTION

Bone tissue, unlike most of the human body's tissues, has the remarkable ability to regenerate itself. If a fractured bone can be held together for a given period of time, it can regenerate the tissue and regain most of its original strength. For various fractures, bone plates are surgically implanted to hold the bone in place. A bone plate is typically a relatively thin metal implant used to immobilise bone segments. The plate comprises holes or perforations for receiving fastening elements, such as screws, so that the plate is affixed with the fastening elements to properly align the bone and aid in the healing process. In spine surgery, a bone plate may be used to help stabilise the fused area and also to prevent dislodgement of the bone graft. It is used most commonly in cervical fusion surgery, i.e. in the neck.

The interface between the screw and the bone plate forms a screw locking mechanism for locking screws and is an important consideration when designing bone plate assemblies. The locking mechanism has a major influence on the plate because it defines the minimal plate thickness. Furthermore, the plate manufacturing costs also directly depend on the plate hole design. In other words, a complex hole design typically increases the manufacturing costs of the plate. The holes can be constructed to receive a non-locking, locking, or variable-angle locking bone screw. Traditionally, the plate holes have discrete columns of teeth or thread segments arranged around the inner surface of the hole for engaging threads on the heads of locking and variable-angle locking bone screws. Conventional locking bone screws engage the bone plate coaxially with the central axis of the bone plate hole. However, variable-angle locking mechanisms allow bone screws to engage the bone plate at a selectable angle within a range of selectable angles relative to the central axis of the bone plate hole. Currently known locking mechanisms typically have some limitations, such as high complexity, limited angle stability, high variation of angle stability, voluminous design, bad usability and/or high screw insertion torque.

Furthermore, when designing bone plates, material selection, is also often an important consideration. The bone plate must be sufficiently strong to support the load normally placed on the bone while the bone heals. Biocompatibility is also an issue when designing bone plates. The implant is preferably non-toxic and should not cause an inflammatory response in the body.

SUMMARY OF THE INVENTION

It is an object of the present invention to overcome at least some of the problems above related to bone plate systems and more particularly to their locking mechanisms.

According to a first aspect of the invention, there is provided a bone plate system as recited in claim 1.

The proposed solution has the advantage that it offers very efficient and inexpensive way of locking fastening elements to a bone plate of the system. Thanks to the simple design of the bone plate and its holes, the manufacturing costs of the plate can be kept low and various manufacturing processes may be used to produce the plates. Further advantages are for example: low risk of producing lack of metal chips when inserting screws into the holes, easy to design the locking mechanism for different dimensions, the fastening elements perform substantially the same manner irrespective of the insertion direction and/or position, easy removal and re-insertion of the fastening elements, very high angle stability and reproducibility for each angle even if the fastening elements are removed and re-inserted optionally at a different angle. Furthermore, by choosing the materials appropriately, a high corrosion resistance can be achieved as well as high surface quality and hardness.

Other aspects of the invention are recited in the dependent claims attached hereto.

BRIEF DESCRIPTION OF THE DRAWINGS

Other features and advantages of the invention will become apparent from the following description of a non-limiting example embodiment, with reference to the appended drawings, in which:

FIG. 5 is a cross-sectional view illustrating in detail one plate hole of the bone plate of the bone plate system of FIG. 1;

FIG. 6 is an isometric view illustrating an example screw of the bone plate system of FIG. 1;

FIG. 7 is a top view of the screw of FIG. 6;

DETAILED DESCRIPTION OF AN EMBODIMENT OF THE INVENTION

Figure 1:
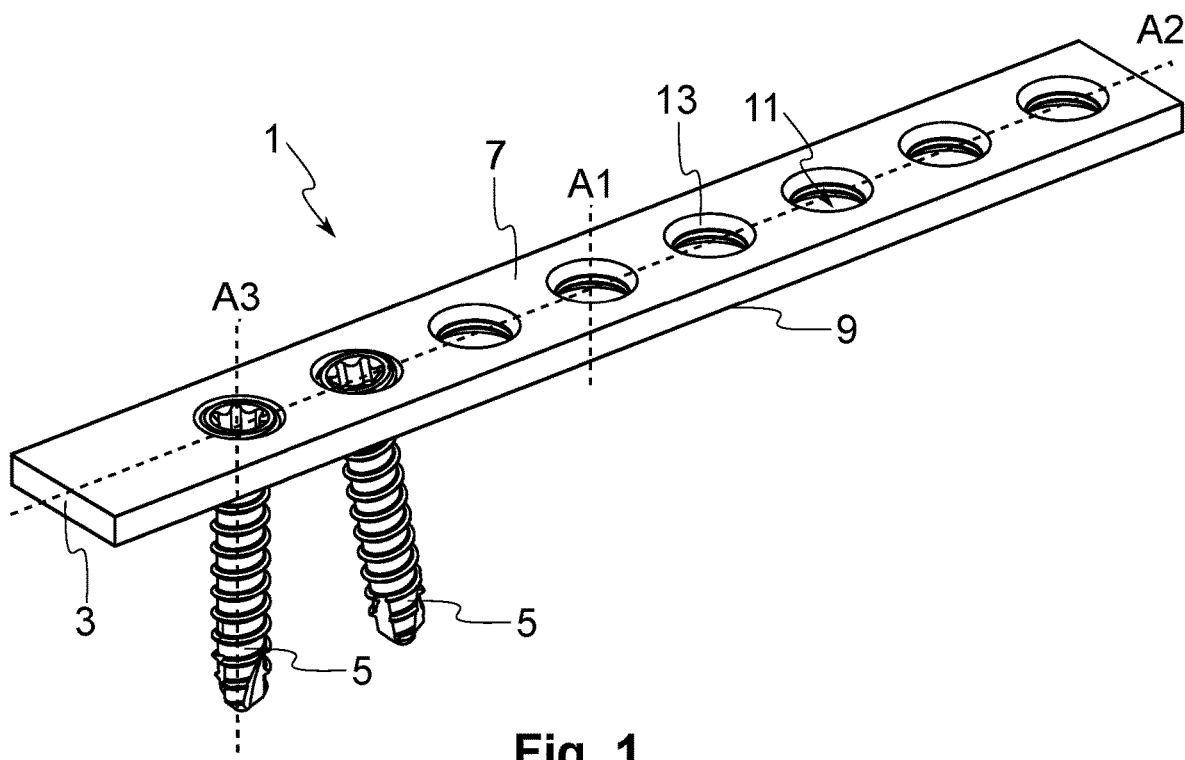
FIG. 1 is an isometric view illustrating the bone plate system according to an example embodiment of the present invention.

An example embodiment of the present invention will now be described in detail with reference to the attached drawings. The embodiment is described in the context of a variable-angle bone plate system or assembly for bridging at least two bone segments. The proposed bone system may be used for instance for trauma, spine and/or craniomaxillofacial (CMF) procedures. However, the teachings of the invention are not limited to this environment or application. Identical or corresponding functional and structural elements which appear in the different drawings are assigned the same reference numerals. As utilised herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." Furthermore, the term "comprise" is used herein as an open-ended term. This means that the object encompasses all the elements listed, but may also include additional, unnamed elements. Thus, the word "comprise" is interpreted by the broader meaning "include", "contain" or "comprehend". A full embodiment of the invention is described next in detail. This description is followed by a description of variants of the present invention.

Figure 2:
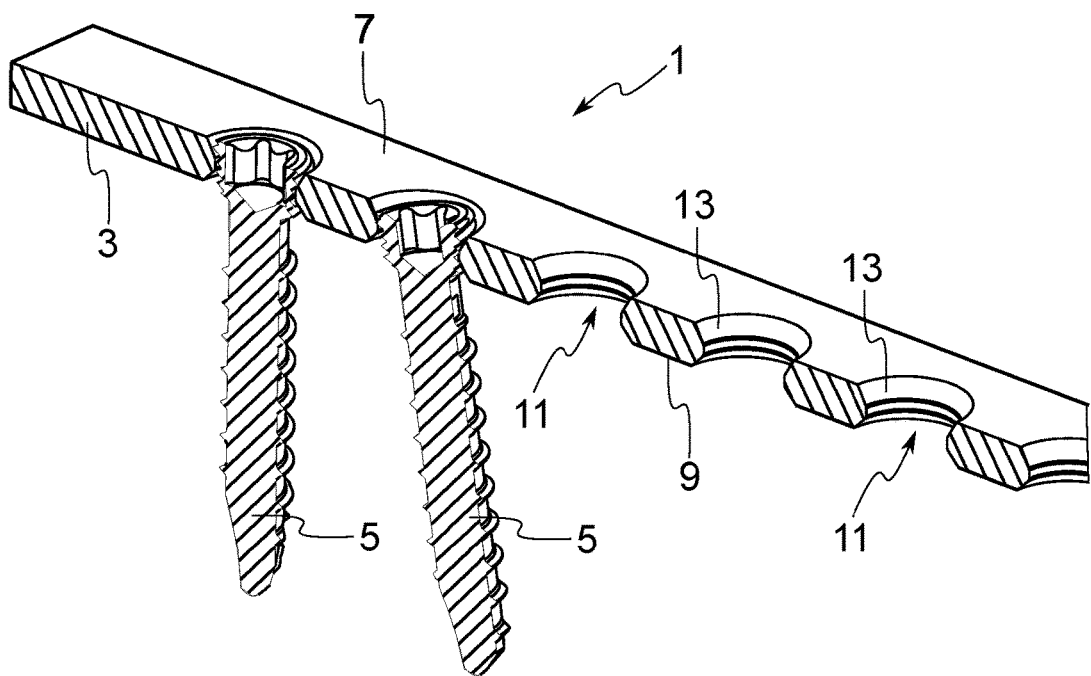
FIG. 2 is a cross-sectional view of a portion of the bone plate system of FIG. 1.

FIGS. 1 and 2 show a bone plate system or assembly 1 according to an example of the present invention. In this example, the bone plate system 1 comprises a bone plate 3 and at least one bone fastening element 5, which in this specific example is a bone screw. In this example, the bone plate 5 has a longitudinal shape with rectangular or substantially rectangular faces, but instead, it could have another shape, such as an element with elliptical or circular faces. The bone plate 3 comprises a first, upper or top surface 7, and an opposing second, lower or bottom surface 9 arranged to be secured to a target bone by means of the one or more screws 5. The bone plate 3 comprises a set of perforations or through plate holes 11 extending between the top and bottom surfaces 7, 9 for receiving the screws 5 (one screw per hole). The holes have a central axis A1 which in this example is substantially orthogonal to a longitudinal axis A2 of the bone plate 3, which is an imaginary straight line passing longitudinally through the bone plate through the centres of the holes 11. In this example, the central axis A1 may be considered to divide the hole or its cross-section into symmetrical halves. The bone plate 3 is in this example a metal plate. It is advantageously made of steel or titanium, but as explained later magnesium or any other suitable material, such as plastic, could be used instead.

Figure 3:
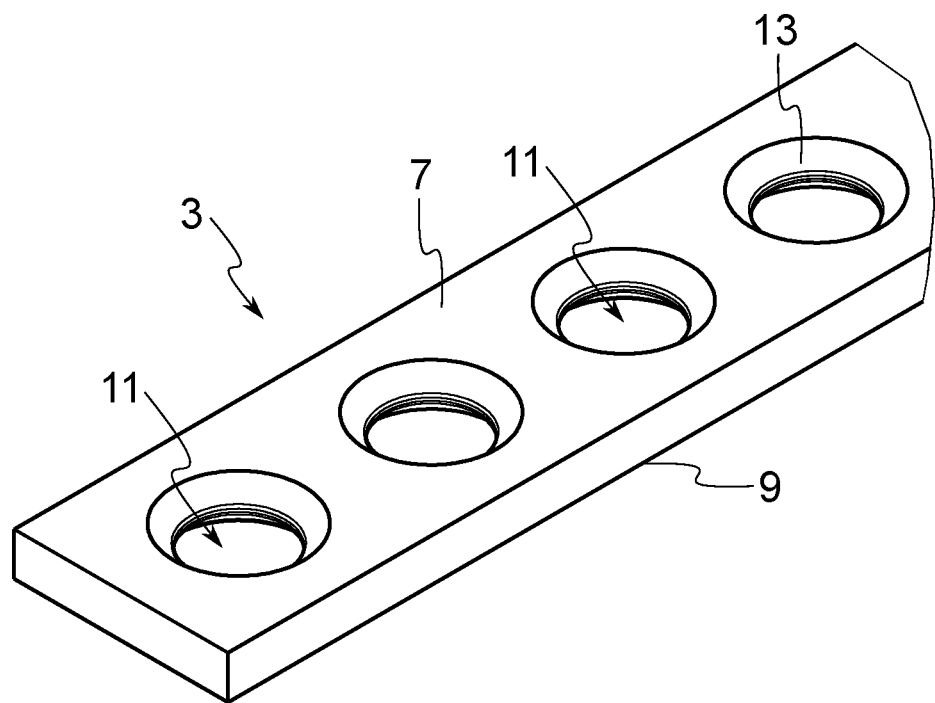
FIG. 3 is an isometric view illustrating a portion of a bone plate of the bone plate system of FIG. 1.
Figure 4:
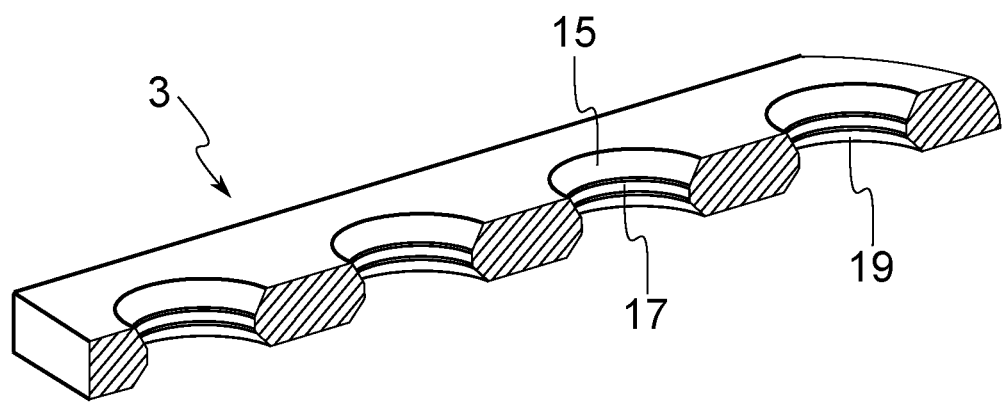
FIG. 4 is a cross-sectional view illustrating a portion of the bone plate of FIG. 3.

In a state, in which no screws have been inserted into the holes, referred to as an unassembled state, the holes have a non-threaded smooth inner surface or wall 13 delimiting the holes. In this example, the holes are rotationally symmetrical around the central axis A1. As better illustrated in FIGS. 3 to 5, in this example, the holes can be divided into three contiguous sections, segments or portions: a first or top portion 15, also referred to as a first tapering portion, a second or middle portion 17 and a third or bottom portion 19, also referred to as second tapering portion. The middle portion is located between the first and second tapering portions. Each of the hole portions defines its own three-dimensional shape or volume or a three-dimensional surface of revolution. All these three shapes may be different (optionally when also considering the orientation of the shape) at least when seen from a fixed reference point or surface, such as the first or second plate surface 7, 9.

In this example, the middle portion defines a cylindrical or substantially cylindrical volume. In this case the diameter of the hole (in the plane defined by the top or bottom surfaces) throughout the middle portion is constant or substantially constant. In this example, the first and second tapering portions 15, 19 define each a segment of a conical or substantially conical volume such that the volumes both taper towards the middle portion. More specifically, in this example, the first and second tapering portions 15, 19 each define a conical frustum. Thus, in the first and second tapering portions 15, 19, the hole diameter becomes progressively smaller or diminishes gradually towards the middle portion 17. Thus, the first and second tapering portions taper in opposite directions. In this example, the plate 3 is rotationally symmetrical. In other words, the hole design is symmetrical with respect to the middle portion 17 or to the longitudinal axis of the plate A2. This also means that instead of the second surface 9 being the bone facing surface, the first surface 7 could be the bone facing surface. In the present example, when the screws 5 are received in the holes 11, they do not protrude from the top surface 7 or protrude only slightly if the screws are inserted into the holes at a non-orthogonal angle with respect to the longitudinal axis A2 of the plate 3.

FIG. 5 shows a more detailed cross-sectional view of the hole 11. FIG. 5 also illustrates how various parameters linked to the hole design are defined in the present text. B denotes the thickness of the plate 3 and thus also the height of the hole in the direction of the central axis A1 (if the central axis A1 is orthogonal to the longitudinal axis A2 of the bone plate). The plate thickness is in the range of 0.5 mm to 20 mm, or more specifically between 1 mm and 10 mm. Advantageously the plate thickness is between 1 mm and 5 mm. The value of the plate thickness may or may not be constant throughout the plate. Thanks to the simple hole design, the plate thickness can be minimised. Furthermore, it is possible to have the holes as close to each other as possible. C denotes the location of the middle plane of the hole 11 in the plate 3 with respect to the top surface 7, i.e. C is the distance of the middle plane from the top surface 7 or top plane. The value of C may be between 0 and B. In the example shown in FIG. 5, C equals B/2.

V denotes the imaginary apex angle of the cone defined by the first tapering portion. In other words, V denotes the opening angle of the first portion 15 towards the top surface 7. The value of V is between 10° and 175° or more specifically between 30° and 120° or more specifically between 60° and 100°. In this specific example, this value is substantially 90° but it has been discovered that a broader range of 70° to 120° also provides very promising results. X is the parameter corresponding to the parameter V but for the second tapering portion 19. Thus, X denotes the opening angle of the third portion towards the bottom surface 9. The parameter X can take the same or different values compared to the parameter V. The purpose of the tapering portions is to allow the user to insert the screw into the hole at a desired angle, which in this example is between 0° and 30° with respect to the central axis A1 of the hole. Thus, this aspect of the present invention enables the bone plate system to be a variable angle bone plate system. The user-defined angle between the screw and the bone plate assembly allows the user to insert a set of fastening elements at variable angles into the bone of a patient. It is to be also noted that although in this example the first and second tapering portions have the same tapering angle, the tapering angle could be different for the first and second tapering portions 15, 19.

Y denotes the height of the middle portion, i.e. Y denotes the dimension of the middle portion in the direction of the central axis A1. This parameter can take different values depending on the screw dimensions but is constant in the present example throughout the middle portion. However, the value of the parameter Y does not have to be constant throughout the middle portion. This value is typically in the range of 0 mm to 5 mm or more specifically between 0.1 mm and 2 mm or more specifically between 0.2 mm and 0.6 mm. D1 denotes the internal diameter of the hole in the middle portion. Also this parameter can vary depending on the screw dimensions. The value of D1 is typically in the range of 1 mm to 15 mm or more specifically between 1 mm and 19 mm or more specifically between 2 mm and 7 mm.

Two screws 5 with a longitudinal axis A3 are shown in FIGS. 1 and 2. However, instead, the number of the screws could be equal to the number of the holes 11. Alternatively, the bone plate system 1 could comprise any number of screws greater than zero. The screw, which is better illustrated in FIGS. 6 to 8 can be divided into two parts or portions, namely a shaft portion 21, or simply a shaft, and a head portion 23 or simply a head. When screwed into the bone plate 3, the head is arranged to be locked or secured in the bone plate 3, while the shaft is arranged to be screwed into the target bone. For this purpose, the shaft 21 comprises on its surface a first outer thread 25. The screw head 23 on the other hand comprises on its outer surface a second outer thread 27 for screwing into the wall of the hole. The shaft 21 has a fluted tip to make the shaft screw thread self-tapping. In other words, the screw 5 has a special point to cut through the bone which eliminates the need for tapping a thread in a pilot hole by other means. In this example, the shaft comprises unthreaded portion between the first and second threads. In this example, the second thread 27 is a multiple start thread and more specifically a triple-start thread, however a single-start, double-start or quadruple-start thread could be used instead. However, it is to be noted that the number of the thread starts could alternatively be more than four. The thread starting points are divided equally around the screw head contour, such that the angular separation between the starting points is given by 360°/(the number of thread starting points). In this example, the first thread is a single-start thread, although multiple start screws could be also or instead used.

Figure 8:
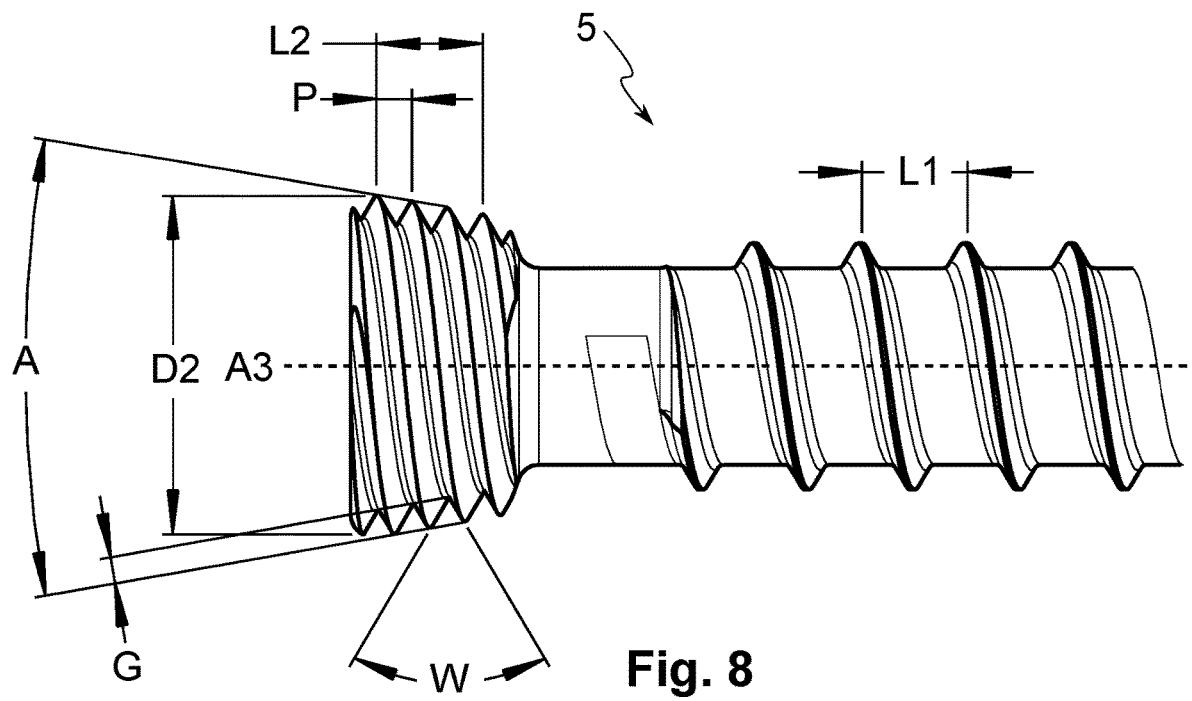
FIG. 8 is a side view of a portion of the screw of FIG. 6.

Some parameters related to the screw design are illustrated in FIG. 8. L1 denotes a first lead length, i.e. L1 is the lead length of the thread of the shaft portion 21. L2 denotes a second lead length, i.e. L2 is the lead length of the thread of the head portion 23. P denotes the pitch of the thread of the screw head portion. Thus, P=L2/(number of thread starts on the screw head). Lead length or simply lead is the linear travel the screw makes per one screw revolution. The pitch and lead are equal with single start screws. For multiple start screws the lead is the pitch multiplied by the number of starts. In the present example, L1 equals L2. In other words, the leads of the threads are the same or almost or substantially the same on the shaft and head. This has the advantage that the screw can be smoothly screwed into the bone and thus any damage caused to the bone tissue can be minimised or avoided. L1 and L2 are in the range of 0.3 mm to 7.5 mm or more specifically between 2.5 mm and 7.5 mm or more specifically between 0.5 and 1.5 mm.

D2 is the screw head diameter or the largest screw head diameter if the screw head diameter is not constant. In this example, D2 is between 1 mm and 15 mm, or more specifically between 1 mm and 10 mm. The angle W denotes the thread angle of the screw head. The thread angle is the angle between the threads. This is a defining factor for the shape of the screw thread. In this example, W is between 10°-170° or more specifically between 20° and 100° or more specifically between 20° and 80°. The angle A of the screw head gives the tapering angle of the conical screw head form. In this example, it is between 0° and 85° or more specifically between 0° and 50° or more specifically between 0° and 30°. It is to be noted that the shape of the screw head does not have to be cylindrical or conical. For example, the side profile of the screw head 23 could be rounded so that the head could be substantially spherical. In other words, the side profile of the screw head could draw an imaginary line representing a portion of a circle or an ellipse. The screw head may be designed depending on the hole dimensions to obtain an optimal locking force. G denotes the depth of the screw head thread and it may vary between 0.1 mm and 3.0 mm or more specifically between 0.1 mm and 1 mm.

It is to be noted that the value of D1 directly influences the design of the screw head, and more specifically the diameter D2. For example, if the value of D1 is increased or decreased by 10%, then the value of D2 would be increased or decreased by 5% to 15% or optionally the same amount as the change of dimension of D1. Also, the values of G and D2 are chosen depending on the value of the height Y of the middle portion, while the values of A and G and W directly depend on the values of V and X. For example, If the value of Y is 0.05 mm-0.7 mm, then the value of G is 0.1 mm-3.0 mm and/or if the value of V and/or X is/are increased or decreased by 10%, then the value of A would be increased or decreased by 5% to 15% or optionally the same amount as the change of dimension of V and/or X. Furthermore, the value of A directly depends on the value of V and C.

The outer surface of the screw 5 or more specifically the outer surface of the head portion 23 is characterised by a first hardness value, while the surface of the hole wall 13 is characterised by a second hardness value so that the first hardness value is greater than the second hardness value. More specifically, the first hardness value and more specifically the indentation hardness value is at least 10%, but more preferably at least 50% or 100% or even 150% greater than the second hardness value. In this example, the bone plate material is made of one single material which means that the hardness value of the bone plate 3 is substantially constant throughout the plate. As far as the screw head is concerned, the outer surface of the head may be of different hardness than the remaining parts of the screw or at least the internal part of the screw. More specifically, the outer surface of the screw head is harder than the remaining parts of the screw or at least harder than the internal part of the screw. Thus, the entire outer surface of the screw or merely the outer surface of the head may be hardened. Hardening, when applied to metals, is a metallurgical metalworking process used to increase the hardness of the metal. The hardness of a material is directly proportional to the uniaxial yield stress at the location of the imposed strain. A harder material has a higher resistance to plastic deformation than a less hard material.

The hardening may be achieved for example by coating the relevant parts of the screw, or by heat treatment or by cold working or forming (also known as work hardening). The cold forming techniques can be classified into four major groups: squeezing, bending, drawing, and shearing. Heat treatment or heat treating, including e.g. case hardening, is a group of industrial and metalworking processes used to alter the physical, and sometimes chemical, properties of a material. The most common application is metallurgical. Case hardening is a thermochemical diffusion process in which an alloying element, such as carbon or nitrogen, diffuses into the surface of a monolithic metal. The resulting interstitial solid solution is harder than the base material thereby improving wear resistance without sacrificing toughness. Other examples of heat treatment processes include carburisation, nitriding or carbonitriding processes. In the present example, only the head 23 of the screw 5 is coated with a layer which is harder than the walls 13 of the holes 11.

The list below gives some examples for the materials of the plate and/or screw and possible hardness values in HV (Vickers number) before the hardening process if used:

Titanium (Ti): 120 HV-500 HV;
Stainless Steel: 120 HV-600 HV;
Cobalt-Chromium-Molybdenum (CoCrMo): 250 HV-550 HV;
Polyether ether keton (PEEK): 20 HV-50 HV;
Ceramic materials: 1000-2500 HV; and
Magnesium.

It is to be noted that any of the above combinations are also possible. As far as the coating of the screw is concerned, the following materials or material combinations are for instance possible: titanium nitride (TiN), titanium aluminium nitride (TiAlN), aluminium titanium nitride (AlTiN), chromium nitride (CrN), titanium carbon-nitride (TiCN), chrome carbon-nitride (CrCN), Cr+a-C:H:W, Cr+a-C:H:W+a-C:H, Cr+CrN+a-C:H, amorphous hydrogenated carbon (a-C:H), tetrahedral amorphous carbon (t-a:C), zirconium nitride (ZrN), molybdenum disulfide ($MoS_2$), titanium (Ti), Nb(X,O). The coating may thus be a diamond-like carbon (DLC) coating, which is a class of amorphous carbon material that displays some of the typical properties of diamond. DLC exists in seven different forms, which all contain a significant number of $sp^3$ hybridised carbon atoms. The reason that there are different types is that diamond can be found in two crystalline polytypes. The more common one has its carbon atoms arranged in a cubic lattice. The less common one, namely lonsdaleite, has a hexagonal lattice. By mixing these polytypes in various ways at the nanoscale level of structure, DLC coatings can be made that at the same time are flexible, amorphous and yet purely $sp^3$ bonded "diamond". The hardest, strongest, and slickest is known as tetrahedral amorphous carbon. The thickness of the coating layer depends on the material used but is generally between 0.3 μm and 30 μm. If the entire screw head is hardened, this would have the additional advantage that the end of the screw head does not wear easily (high fretting resistance) when a screw driving means, such as a screw driver, is connected to it to rotate the screw 5. The following coating hardness values may for example be reached: TiN: 2700 HV-3100 HV, TiCN: 2800 HV and DLC: 2000 HV-2800 HV. Thus, the coating hardness may be at least 2000 HV. If stainless steel is hardened, then a hardness value of about 900 HV could be obtained.

Thanks to the hardness difference between the hole walls 13 and the outer surface of the screw head, it is possible for the screw thread of the head to form a female thread directly on the hole walls when inserting the screw into the bone. More specifically, the second thread 27 irreversibly deforms the wall to form an internal thread on the wall 13. This means that when removing the screw from the bone and thus also from the bone plate 3, the formed thread remains on the wall 13, i.e. the wall does not reversibly deform once the screw has been removed from the hole 11. This means that the material of the plate (e.g. metal) is not susceptible to elastic deformation. Thus, the screws used in the present invention and which are arranged to tap a thread on the wall 13 can be called self-tapping screws. They may additionally be self-drilling. The thread is formed by the screw in the second hole portion 15, i.e. in the middle portion. However, depending on the screw insertion angle, a part of the thread may also be formed in the first and third hole portions 15, 19 close to the second portion 17. It is further to be noted that, the present invention does not need any inlay placed in the holes between the screw 5 and the wall 13. Thus, an inlay-free locking mechanism is proposed.

Figure 9:
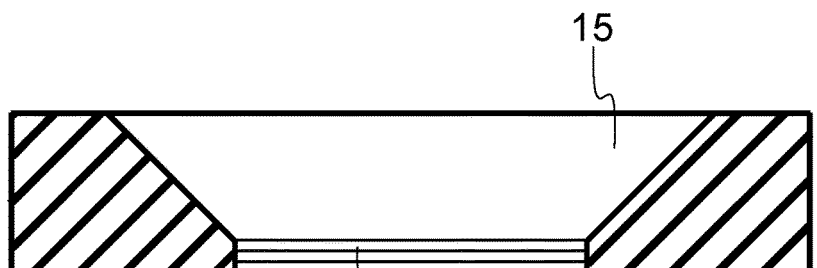
FIGS. 9 to 15 are cross-sectional views showing variants of the plate holes.
Figure 10:
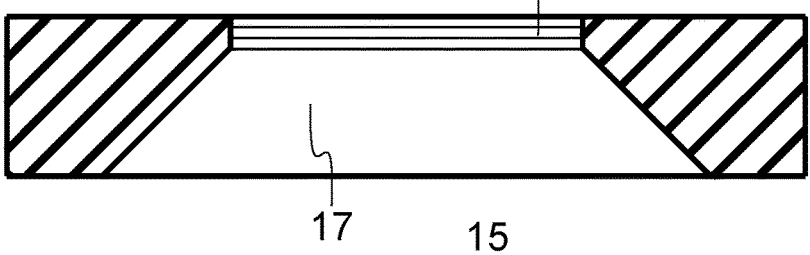

FIGS. 9 to 15 show variants of the hole design. FIG. 9 illustrates a design in which the hole 11 comprises only two contiguous hole portions, namely the first tapering portion 15 and the middle portion 17. In other words, in this variant the hole(s) comprise(s) only two contiguous portions, but no third portion. The second portion would in fact reach the bone facing surface 9. The design of FIG. 10 differs from the design of FIG. 9 in that the plate has been flipped upside down, i.e. it has been rotated 180°. In this design, the only tapering portion opens towards the bone facing surface of the plate 3.

Figure 11:
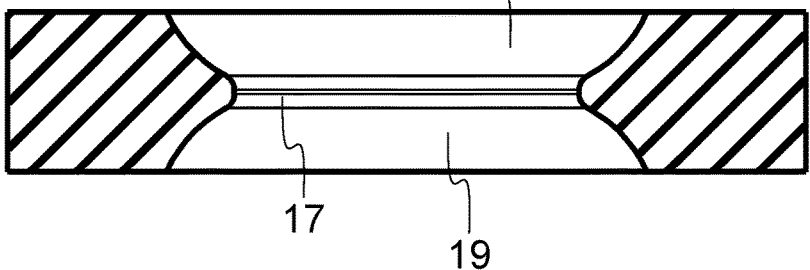
Figure 12:
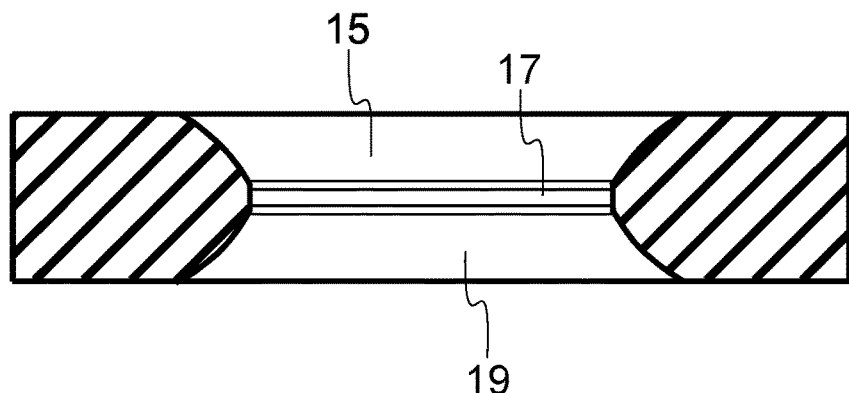
Figure 13:
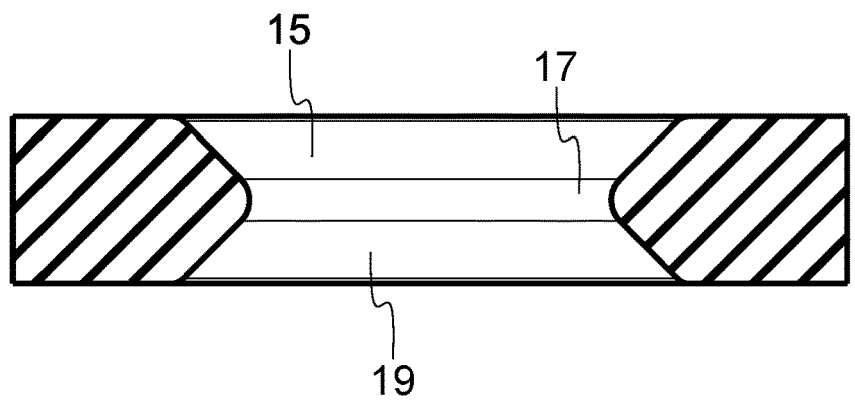
Figure 14:
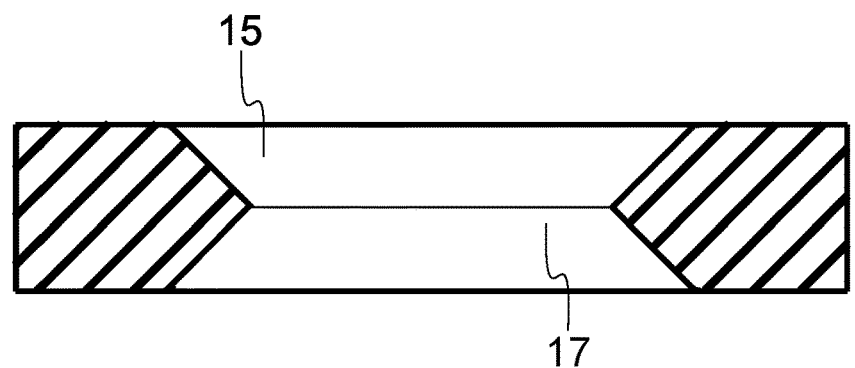
Figure 15:
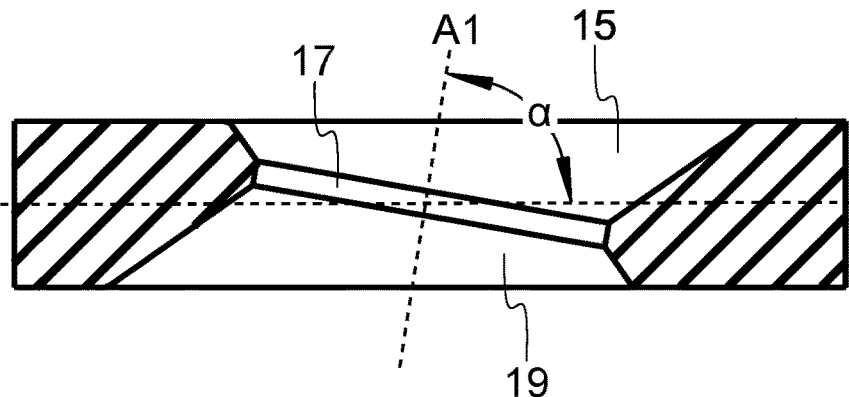

In the variants of FIGS. 11 and 12, the cross section of the hole has rounded walls as opposed to being straight. In the variant of FIG. 11, the tapering portions define a three-dimensional shape, which is a spherical segment (corresponding to a spherical frustum) or a segment of an ellipsoid. In the variant of FIG. 12, the tapering portions are segments of a hyperboloid. In the variant of FIG. 13, the cross section of the middle portion has rounded walls. In other words, the middle portion 17 defines a three-dimensional shape, which is in this example is a segment of a hyperboloid. However, it could instead be a segment of a sphere or a segment of an ellipsoid. In the variant of FIG. 14, there is no middle portion, or it can be considered to be simply a sharp edge between the first and second tapering portions 15, 19, i.e. a very narrow segment comprising the ends of the two tapering portions thus defining a double conical frustum. FIG. 15 illustrates yet another variant. In this variant the central axis A1 of the hole 11 is angled with respect to the longitudinal axis of the plate A2. In other words, the central axis A1 as shown in FIG. 15 is non-orthogonal with respect to the longitudinal axis A2 of the bone plate 3. The hole may be angled between 5° and 90° (angle α in FIG. 15) with respect to the longitudinal axis A2 of the bone plate 3. However, angles between 50° and 90° are particularly advantageous when securing the screws 5 into the bone. It is to be noted that further variants may be obtained by combining the teachings of at least two different hole designs. For example, the first and second tapering portions may form three-dimensional shapes of different shapes, e.g. one volume could be a spherical segment while the other could be a segment of a hyperboloid etc.

Figure 16:
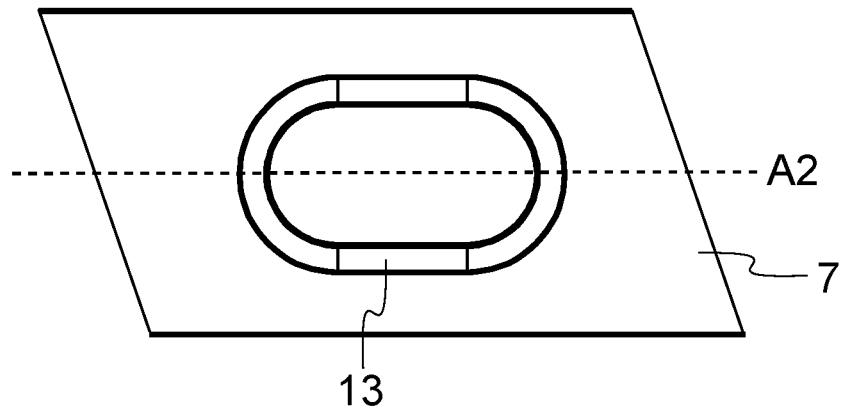
FIGS. 16 to 18 are top views showing further variants of the plate holes.
Figure 17:
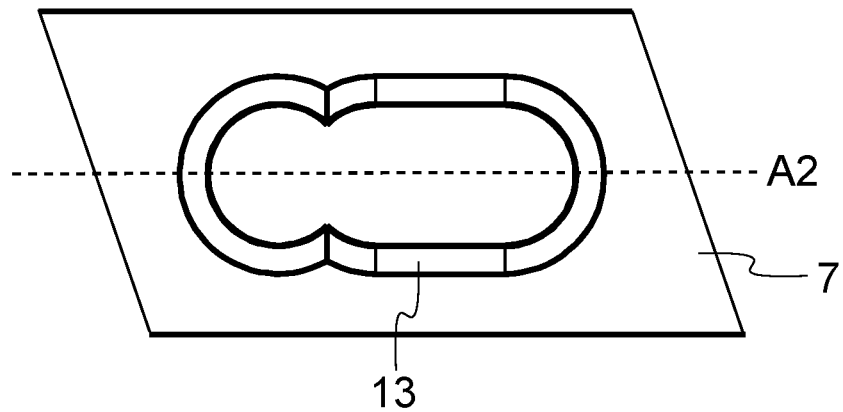
Figure 18:
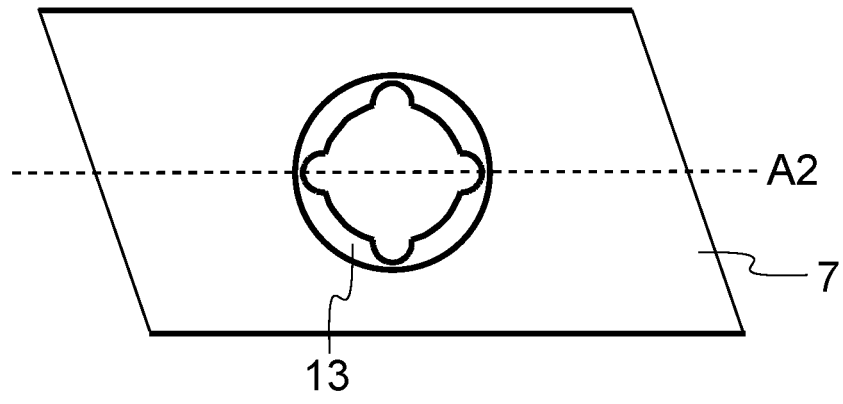

FIGS. 16 to 18 show further variants of the hole design. In these designs the holes 11 are not rotationally symmetrical around the hole axis A1. In the variant of FIG. 16, the hole 11 is a longitudinal hole so that in this example the hole extends longitudinally in the direction of the longitudinal axis of the plate A2. The screw can be positioned at any position along the length of the hole and then locked in place at any desired angle. The hole 11 of FIG. 17 is also a longitudinal hole but additionally the hole can be longitudinally divided into two distinct sections, which are a partly circular section and a longitudinal section separated by a narrowing portion or waist portion. These two sections have their own hole central axis. These two axes may or may not be parallel. The screw 5 is arranged to longitudinally move in the longitudinal section before the screw is locked in place similar to the design of FIG. 16. The design of FIG. 18 has a 4-point star-shaped pattern. However, a 6-point star-shaped pattern or any other number of points could also be possible. More broadly, the cross-sectional shape of the hole 11 may be symmetrical or non-symmetrical divided by points or other forms, such as recesses. In other words, the first, second and third portions 15, 17, 19 may be broken and not continuous. This means that the cross-sectional width (in the plane of the top and/or bottom surfaces(s) 7, 9) of these three portions may not be constant. In all these designs, the hole cross-section orthogonal to the plate top and/or bottom surface(s) 7, 9 can have any shape mentioned above or any of their combination.

Thanks to the simple plate design, the manufacturing costs of the plate can be kept low. Furthermore, thanks to the simple design, various manufacturing methods are possible. Examples of different manufacturing processes are (metal) injection moulding, 3D printing, stamping, forming, turning, rolling, grinding, forging, drilling and milling. Thus, one aspect of the present invention relates to a manufacturing process or method of the bone plate system. According to this aspect, the bone plate 3 and the fastening element 5 are manufactured by using for instance at least one of the above processes. The process also involves hardening at least the outer surface of the head 23 and in this manner also the second outer thread 27.

While the invention has been illustrated and described in detail in the drawings and foregoing description, such illustration and description are to be considered illustrative or exemplary and not restrictive, the invention being not limited to the disclosed embodiment. Other embodiments and variants are understood, and can be achieved by those skilled in the art when carrying out the claimed invention, based on a study of the drawings, the disclosure and the appended claims. For example, one single bone plate 3 could have any combination and number of different holes 11 as explained above. The number of the holes 11 per bone plate may be for example between 1 and 20 or more specifically between 1 and 10.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. A bone plate system for securing a bone plate to a bone, the bone plate system comprising:
    a bone fastening element comprising a shaft with a first outer thread with a first lead length for securing the fastening element to the bone, the fastening element further comprising a head with a second outer thread on its outer surface, the second outer thread having a second lead length, the outer surface having a first hardness; and
    a bone plate comprising a non-threaded through hole in a non-assembled state for receiving the bone fastening element to form an assembled state, the hole being delimited by a hole wall with a second hardness, the first hardness being greater than the second hardness, the hole extending through the bone plate from a first plate surface to a second, opposing plate surface forming a bone facing surface, the hole comprising a first hole portion defining a first three-dimensional shape and a second hole portion defining a second, different three-dimensional shape such that in at least one of the hole portions an internal hole diameter increases towards the first or second plate surface,
    wherein the first lead length substantially equals the second lead length, and wherein the second outer thread is arranged to irreversibly deform the wall to form a female thread on the wall, and wherein the first hardness of the outer surface of the head is greater than a third hardness of an interior portion of the head.

2. The bone plate system according to claim 1, wherein the first hole portion defines one of the following shapes: a conical frustum, a spherical segment, an ellipsoidal segment and a hyperboloidal segment.

3. The bone plate system according to claim 1, wherein in the second hole portion the internal hole diameter is substantially constant.

4. The bone plate system according to claim 3, wherein the second hole portion has a substantially cylindrical shape.

5. The bone plate system according to claim 1, wherein the bone plate further comprises a third hole portion with a third three-dimensional shape, which is different from the second three-dimensional shape, and wherein in the third hole portion the internal hole diameter increases towards the first or second plate surface such that in one of the first and third hole portions the internal hole diameter increases towards the first plate surface, while in the other hole portion of the first and third hole portions the hole diameter increases towards the second plate surface.

6. The bone plate system according to claim 5, wherein the third hole portion defines one of the following shapes: a conical frustum, a spherical segment, an ellipsoidal segment and a hyperboloidal segment.

7. The bone plate system according to claim 1, wherein the through hole defines a central axis, and wherein the second hole portion has a height of 0.2 mm to 0.6 mm measured along the central axis and/or the bone plate has a thickness between 1 mm and 5 mm.

8. The bone plate system according to claim 1, wherein the first outer thread has a first pitch, while the second outer thread has a second pitch, different from the first pitch.

9. The bone plate system according to claim 1, wherein the first hardness is at least 10% greater than the second hardness and more preferably at least 50% greater.

10. The bone plate system according to claim 1, wherein the outer surface of the head comprises a coating or is carburised, nitride and/or carbonitrided.

11. The bone plate system according to claim 10, wherein the coating is of at least one of the following materials: titanium, titanium nitride, titanium aluminium nitride, aluminium titanium nitride, chromium nitride, chrome carbonitride, zirconium nitride, molybdenum disulfide and a diamond-like carbon.

12. The bone plate system according to claim 1, wherein the bone plate is rotationally symmetric with respect to a longitudinal axis of the bone plate.

13. The bone plate system according to claim 1, wherein the first hardness is at least 400 HV or more specifically at least 1200 HV or at least 2000 HV.

14. The bone plate system according to claim 1, wherein the through hole defines at least one central axis, which is non-orthogonal with respect to the first or second plate surface.

15. The bone plate system according to claim 1, wherein the hole defines a central axis, and wherein the hole is rotationally non-symmetrical around the central axis.

\* \* \* \* \*